(12) United States Patent
Faccioli et al.

(10) Patent No.: US 9,173,742 B2
(45) Date of Patent: Nov. 3, 2015

(54) MODULAR SPACER DEVICE FOR THE TREATMENT OF PROSTHESIS INFECTIONS

(75) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 392 days.

(21) Appl. No.: 12/293,665

(22) PCT Filed: Aug. 6, 2008

(86) PCT No.: PCT/IB2008/002072
§ 371 (c)(1),
(2), (4) Date: Sep. 19, 2008

(87) PCT Pub. No.: WO2010/015877
PCT Pub. Date: Feb. 11, 2010

(65) Prior Publication Data
US 2011/0118848 A1 May 19, 2011

(51) Int. Cl.
*A61F 2/36* (2006.01)
*A61F 2/38* (2006.01)
*A61F 2/40* (2006.01)
*A61F 2/30* (2006.01)

(52) U.S. Cl.
CPC ... *A61F 2/38* (2013.01); *A61F 2/36* (2013.01); *A61F 2/40* (2013.01); *A61F 2002/3055* (2013.01); *A61F 2002/3092* (2013.01); *A61F 2002/30405* (2013.01); *A61F 2002/30448* (2013.01); *A61F 2002/30616* (2013.01); *A61F 2002/30672* (2013.01); *A61F 2002/30677* (2013.01); *A61F 2002/365* (2013.01); *A61F 2310/00353* (2013.01)

(58) Field of Classification Search
CPC .................. A61F 2002/3647; A61F 2002/3645
USPC ............ 623/22.11, 22.4–22.46, 23.19, 19.11, 623/19.14, 23.11–23.12, 23.14
See application file for complete search history.

(56) References Cited

U.S. PATENT DOCUMENTS 3,102,536 A * 9/1963 Rose et al. .................... 623/22.4
3,987,499 A * 10/1976 Scharbach et al. .......... 623/17.11
(Continued)

FOREIGN PATENT DOCUMENTS

EP 1166724 1/2002
EP 1274374 1/2003
(Continued)

*Primary Examiner* — Thomas J Sweet
*Assistant Examiner* — Megan Wolf
(74) *Attorney, Agent, or Firm* — Tutunjian & Bitetto, P.C.

(57) ABSTRACT

A spacer device (1) for the two-step treatment of prosthesis infections, made from biologically compatible and porous material designed to allow the possibility of adding pharmaceutical products, active and/or therapeutic ingredients, includes a first portion (2) designed to be fixed to a corresponding bone bed remaining from a previous implant, and a second portion (3) designed to be inserted in a corresponding articular area of the patient, the first portion (2) and the second portion (3) being attached by adjustable connecting means (4).

18 Claims, 4 Drawing Sheets

(56) References Cited

U.S. PATENT DOCUMENTS

| | | | | |
|---|---|---|---|---|
| 5,645,600 A | * | 7/1997 | Bimman | 623/22.44 |
| 5,800,554 A | * | 9/1998 | Scholz | 623/22.43 |
| 6,533,816 B2 | * | 3/2003 | Sklar | 623/13.14 |
| 7,144,427 B2 | * | 12/2006 | Southworth | 623/22.13 |
| 7,842,095 B2 | * | 11/2010 | Klein | 623/23.19 |
| 2001/0051831 A1 | * | 12/2001 | Subba Rao et al. | 623/22.42 |
| 2004/0054417 A1 | * | 3/2004 | Soffiati et al. | 623/20.31 |
| 2007/0222114 A1 | | 9/2007 | Ziran et al. | |

FOREIGN PATENT DOCUMENTS

| | | |
|---|---|---|
| FR | 2898039 | 9/2007 |
| IT | 1278853 | 9/1995 |
| IT | 1278853 | 11/1997 |
| WO | WO0176512 | 10/2001 |
| WO | WO2007099232 | 9/2007 |

* cited by examiner

MODULAR SPACER DEVICE FOR THE TREATMENT OF PROSTHESIS INFECTIONS

TECHNICAL FIELD

This invention concerns a spacer device for a two-step treatment of prosthesis infections, for example hip prostheses, humerus prostheses, knee prostheses, ankle prostheses, etc.

BACKGROUND ART

Prosthesis infections are one of the most feared reasons for failure of a prosthesis. With specific reference to hip prostheses, these infections are a fairly frequent occurrence with a percentage varying between 0.5% and 6% of cases. The percentage of infections increases in the event of re-implants or in the presence of risk factors such as previous surgery, local hematomas, intercurrent infectious diseases, local or general bone diseases, impaired immunity system, etc.

One method of curing the infection, defined as a two-step treatment, consists of a first step in which the infected prosthesis is removed, since the probability of mere conservative antibiotic treatment being successful is extremely limited, and a second step in which a new prosthesis is implanted once all the infection has been eliminated from the patient's tissues.

In order to maintain the space necessary for the new prosthesis implant and to cure the infection, the applicant has developed special prostheses for temporary use, also called temporary spacers, which release pharmaceutical and/or therapeutic products and permit articular mobility.

These spacers are the subject of the Italian patent no. IT-1278853 and of the European patent no. EP-1274374 in the name of the same applicant and incorporated herein by reference for all purposes.

The international patent application WO-2007/099232 describes a temporary spacer which comprises a semispherical (hemispherical) head which is inserted in the corresponding joint and which can be separated from and attached to a rod to be inserted in the bone bed remaining from the previous implant. With the spacer described in WO-2007/099232, it is possible to combine a rod with different sized semispherical heads in order to adapt to the anatomy of the patient's joint. The connection between the semispherical head and the rod is achieved by means of corresponding truncated cone areas.

SUMMARY OF THE INVENTION

One aim of this invention is to improve the background art.

Another aim of the invention is to provide a spacer device which can be easily adapted to different patient sizes.

A further aim of the invention is to provide a spacer device which is easily implanted in the patient.

Yet another aim of the invention is to produce a spacer device which allows articular function to be maintained, reducing patient recovery times.

An additional aim of the invention is to provide a spacer device that also supports dynamic loads, at least for a certain period of time, while waiting for the definitive re-implant.

In accordance with one aspect of the invention, a spacer device according to claim 1 is envisaged.

BRIEF DESCRIPTION OF THE DRAWINGS

Further characteristics and advantages of the invention will become clearer from the description of some embodiments of the invention, illustrated as examples in the accompanying drawings in which.

EMBODIMENTS OF THE INVENTION

Figure 1:
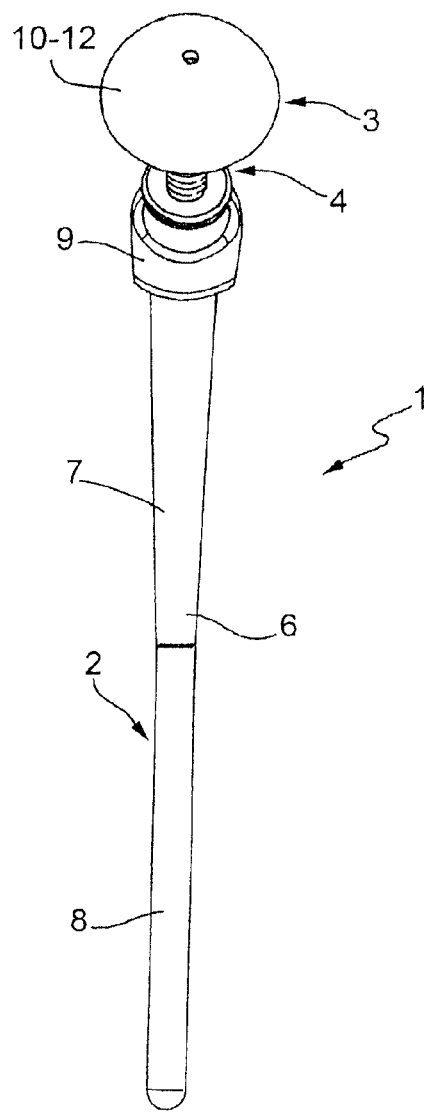
FIG. 1 is a front view of a spacer device according to the invention.

With reference to the figures, the number 1 indicates overall a spacer device according to this invention, in particular a spacer device for the two-step treatment of prosthesis infections.

In the embodiment described, specific reference will be made to a spacer for the treatment and replacement of a hip prosthesis, although it is understood that this invention can also be used to treat other types of prostheses, for example, humerus prostheses, knee prostheses, ankle prostheses, etc. The device 1 according to the invention is made from biologically compatible material which is porous and is designed to allow the addition of one or more pharmaceutical products, active and/or therapeutic ingredients which are released into the patient's tissues adjacent to the device. The materials for the spacer device according to this invention can be chosen from metals, metal alloys, organic metals, ceramics, glass and plastic.

More specifically, plastic can be chosen from thermoplastic polymers, such as acrylic resins, including all the copolymers and acrylic alloys, polyethylene, polypropylene heat-formed by injection moulding or by molding with blowing. In one embodiment of the invention, the material is obtained from a combination of bone cement and one or more of the above-mentioned plastics. The material of the spacer device according to the invention can already comprise one or a plurality of first pharmaceutical products, active and/or therapeutic ingredients, for example antibiotics, and, being porous, one or more pharmaceutical products, active and/or therapeutic ingredients which are the same as or different to the first pharmaceutical products, active and/or therapeutic ingredients, can also be added, for example by impregnation. In another embodiment of the invention, the spacer does not comprise pharmaceutical products, active and/or therapeutic ingredients and one or more pharmaceutical products, active and/or therapeutic ingredients are added, for example by impregnation, when the device is implanted in the patient. From the point of view of the pharmaceutical and therapeutic products, at least three different types of material are therefore possible for the spacer:

a material which already comprises one or a plurality of pharmaceutical products, active and/or therapeutic ingredients without the possibility of adding other pharmaceutical and/or therapeutic products;

a material which already comprises one or a plurality of pharmaceutical products, active and/or therapeutic ingredients with the possibility of adding other pharmaceutical and/or therapeutic products, for example by impregnation when the material itself is porous;

a material which does not comprise any pharmaceutical products, active and/or therapeutic ingredients with the possibility of adding one or a plurality of pharmaceutical products, active and/or therapeutic ingredients when the device is implanted in the patient, for example by impregnation, when the material itself is porous.

The pharmaceutical products, active and/or therapeutic ingredients can comprise antibiotics, antiseptics, antimycotics, chemotherapy drugs, for example gentamicin, vancomycin, etc., or other active ingredients.

According to the figures, the device 1 comprises a first portion 2 designed to be fixed to a corresponding bone bed remaining from a previous implant, a second portion 3 designed to be inserted in a corresponding articular area in the patient, the first portion 2 and the second portion 3 being joined by adjustable type connecting means 4. The device also comprises blocking means 5 designed to fix the position of the adjustable connecting means 4.

In the embodiments shown in the figures, which refer to the hip joint, the first portion 2 comprises a rod 6 to be inserted in the proximal part of a femur.

Figure 2:
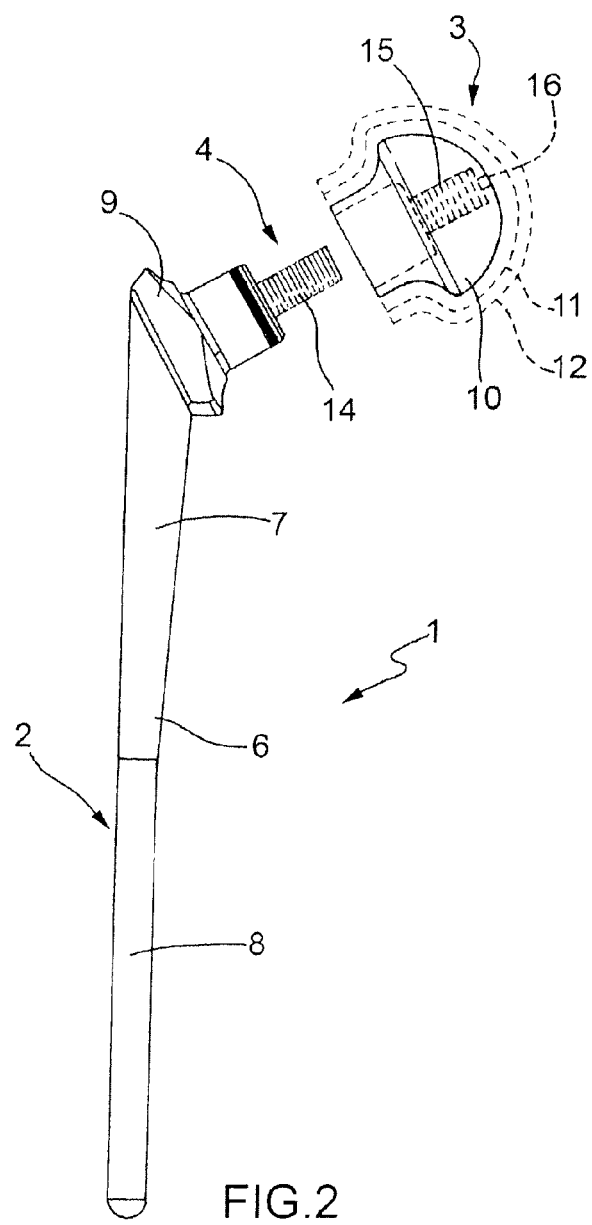
FIG. 2 is a side view of the spacer device shown in FIG. 1.
Figure 3:
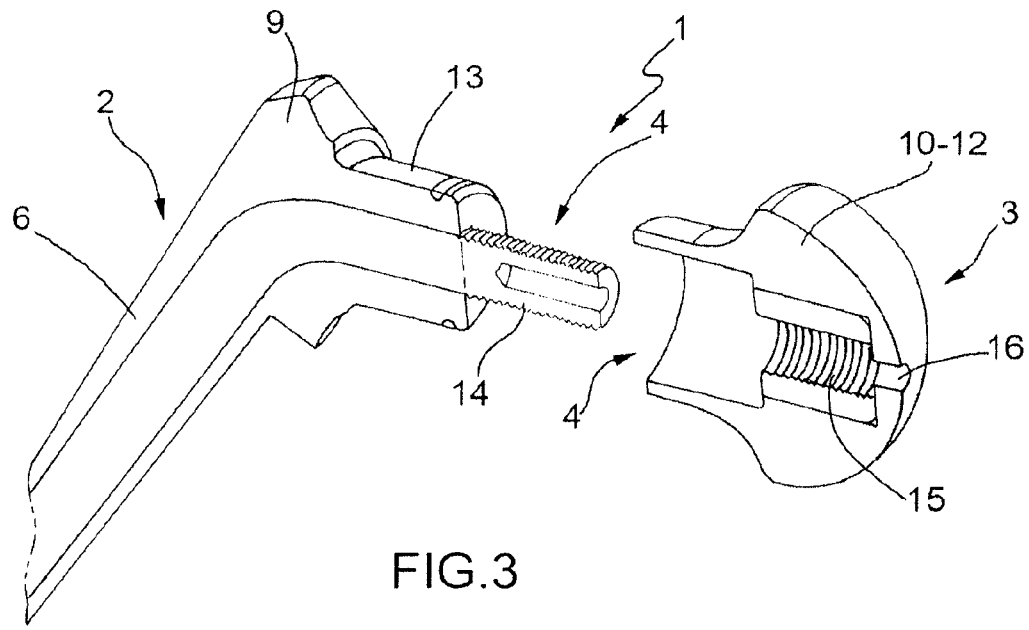
FIG. 3 is a prospective, enlarged and cross-section view of the spacer device shown in the previous figures.
Figure 4:
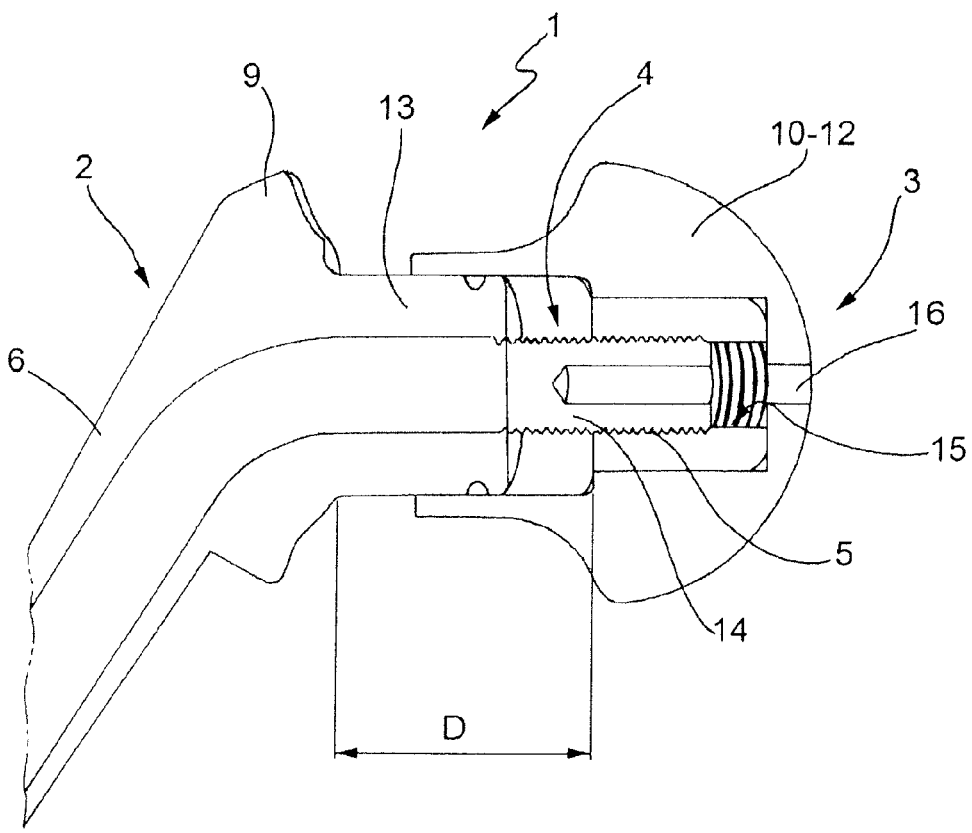
FIG. 4 is a side, enlarged and cross-section view of the spacer device shown in FIG. 3.

According to what is specifically shown in FIGS. 1 and 2, the rod 6 can comprise two fairly long and thin portions 7 and designed to be inserted in a corresponding part of the anatomically long and thin part of the femur. When the femur is thicker and shorter, a wider and shorter rod 6 can be used, like the one shown in FIG. 8.

Figure 7:
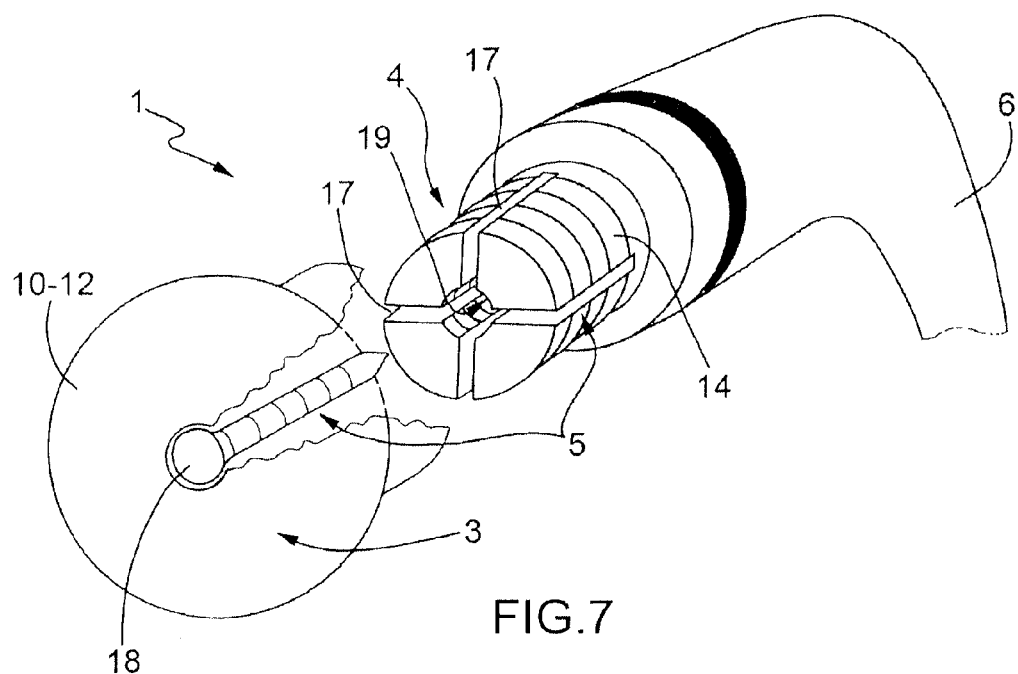
FIG. 7 is a prospective view of another version of the spacer device according to this invention.
Figure 8:
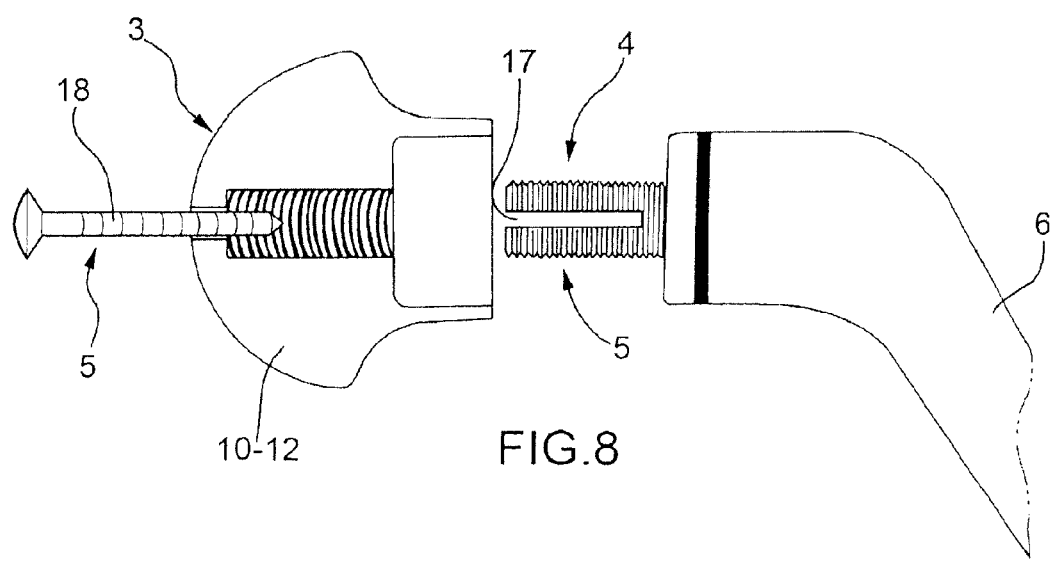
FIG. 8 is a side, enlarged and partial cross-section view of the version of the spacer device shown in FIG. 7.

The rod 6 also comprises a wider portion 9; however, as shown in FIGS. 7 and 8, this wider portion 9 can be absent and the rod 6 can have a substantially truncated cone shape in order to maintain the trochanter of the femur when it is still in good condition.

Again, in the embodiments shown in the figures, the second portion 3 comprises a substantially semisperical head 10, and in particular according to FIG. 2, different sized heads 11, 12 can, for example, be foreseen, in particular with a different diameter of the semisphere in order to adapt to the different sizes of the patients' articular capsules.

It should therefore be noted that it is possible to select different sizes of rods 6, that is to say, rods with different lengths and cross-sections, and different sizes of heads 10-12, in order to adapt better to the patient's anatomy.

An important characteristic of the spacer device according to this invention includes the adjustable connecting means 4 which, in addition to connecting the first portion 2 and the second portion 3, can also be used to adjust the reciprocal position between the first portion 2 and the second portion 3.

In the embodiment shown in the figures, thanks to the adjustable connecting means 4, it is possible to vary the length "D" of the neck 13 of the spacer 1, yet again to adapt better to the anatomy of the patient in whom the spacer device is implanted.

According to a version of the invention, the adjustable connecting means 4 comprise a screw/nut screw connection 14-15, but other types of adjustable connections can also be used, without departing from the scope of the invention. This characteristic constitutes an absolute novelty since it offers the physician the possibility of therapeutically controlling the distraction of the articular heads. In fact, by turning the semispherical head it is possible to lengthen or shorten the neck of the device, making it possible for the physician to achieve the ideal detraction of the articular heads for more appropriate application of the definitive prosthesis.

In other words, when the spacer device is implanted, the physician can decide on the most appropriate length "D" of the neck to maintain the articular heads at a correct distance apart for the subsequent application of the definitive prosthesis.

Figure 5:
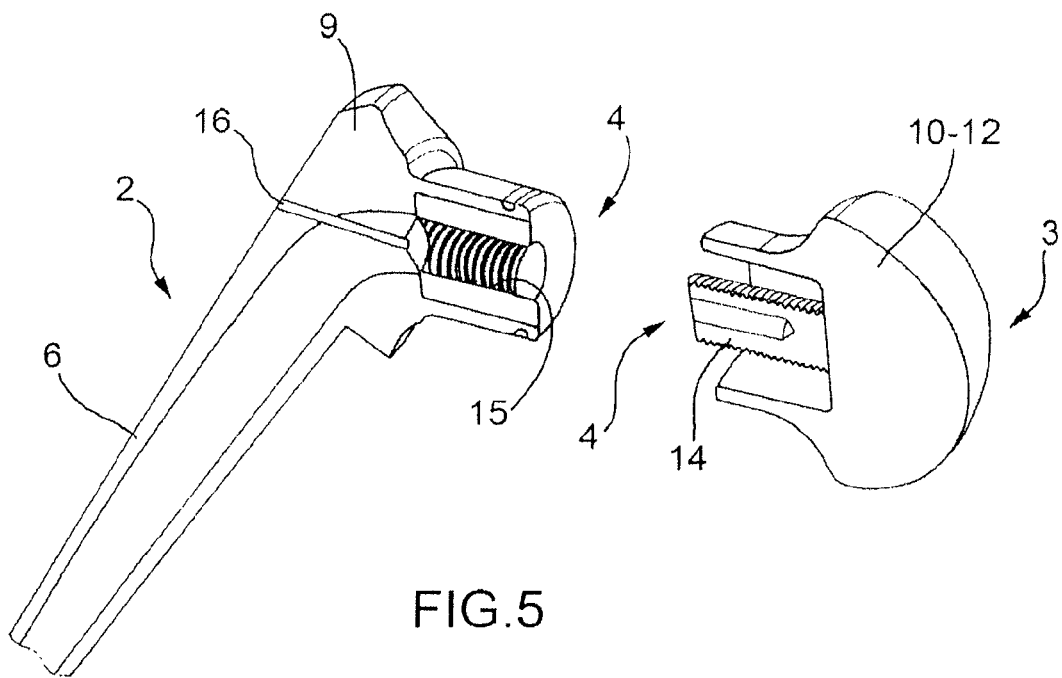
FIG. 5 is a prospective, enlarged and cross-section view of another version of the spacer device according to this invention.
Figure 6:
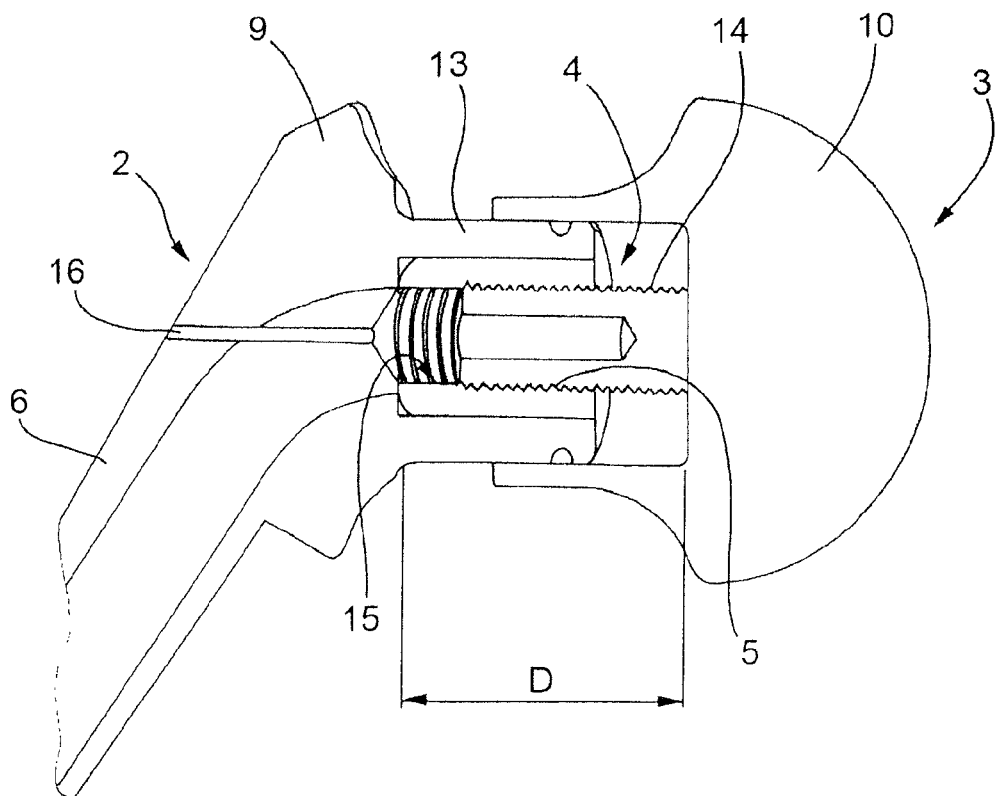
FIG. 6 is a side, enlarged and cross-section view of the spacer device shown in FIG. 5.

In the version shown in FIGS. 1-4 and 7, 8, the screw is supported by the rod 6, while the nut screw 15 is located in the head 10. In the version in FIGS. 5 and 6 the nut screw 15 is located on the rod 6, while the screw 14 is attached to the head 10.

Another important characteristic of the spacer device according to the invention includes blocking means 5 which, according to the embodiment shown in FIGS. 1-6, includes a self-hardening liquid cement designed to fix the reciprocal position between the first portion 2 and the second portion 3.

The blocking means 5 according to the embodiment shown in FIGS. 7-8 comprises a series of grooves, located in a screw and parallel to an axis of the screw itself, and a nail to be inserted in a hole located in the screw, said nail being designed to expand said screw and block the screw in a nut.

A hole or channel 16 may be located in either the first portion 2 or said second portion 3 and enable cement to be injected therein.

In particular, the aforesaid cement prevents the reciprocal rotation between the two portions 2 and 3, that is to say the head 10-12 and the rod 6. The cement, which can be supplied in kit form with special pre-loaded syringes, is injected through a hole or channel 16 which, according to the embodiments of this invention, can be located on the head 10-12 or on the rod 6.

In the version shown in FIGS. 7 and 8, the blocking means 5 comprise a series of grooves 17 located in the screw 14 parallel to the axis of the screw 14 itself and a nail 18, or a screw, to be inserted in a special axial hole 19 in the screw 14. Once the position between the head 10-12 and the rod 6 has been adjusted, the nail 18 is inserted in the hole 19 in the screw 14, and, thanks to the grooves 17, the screw 14 expands and is blocked inside the nut screw 15.

The invention as described above is susceptible to numerous modifications and variations, all of which lie within the protective scope of the claims.

The invention claimed is:

1. A spacer device for treatment of prosthesis infections comprising:
   a first portion designed to be fixed to a corresponding bone bed, said first portion including
   a neck having a threaded cavity, the threaded cavity having an opening and an opposing end portion; and
   a hole formed in the first portion and communicating with the threaded cavity for injection of cement therethrough;
   a second portion designed to be inserted in a corresponding articular area of a patient, said second portion including an elongate hollow portion extending axially from a bottom of the second portion and being configured for receiving the neck;
   said first portion and said second portion being attached by a screw and nut screw connection for providing adjustment between the first and second portions in an axial direction, and wherein the hole formed in the first portion is adapted to enable access from an outer surface of the first portion to the end portion of the threaded cavity of the neck when the first and second portions are attached,
   wherein an inner surface of the elongate hollow portion is configured to be in contact with and is slidable in at least an axial direction relative to an outer surface of the neck.

2. A device according to claim 1, comprising blocking means designed to block a position of the screw and nut screw connection and thus a reciprocal position between the first and second portions.

3. A device according to claim 2, in which said blocking means includes a cement designed to block the reciprocal position between the first portion and the second portion.

4. A device according to claim 1, in which said first portion comprises a rod to be inserted in the proximal part of a femur.

5. A device according to claim 1, in which said first portion can have different lengths and cross-sections to adapt to different sizes of a patient's femur.

6. A device according to claim 1, in which said second portion comprises a substantially semi-spherical head, wherein said head can have various sizes and different diameters to adapt to different sizes of the patient's articular capsules.

7. A device according to claim 1, further comprising a length "D", between a wider portion of said first portion and a base of the second portion, in which the screw and nut screw connection permits adjustment of said length "D".

8. A device according to claim 1, in which the nut screw is attached to the first portion and the screw is located on the second portion.

9. A device according to claim 1, in which said first portion comprises a rod which is substantially a truncated cone shape to maintain a trochanter of a femur on which said rod is to be implanted.

10. A device according to claim 1, in which said device is made from biologically compatible material, said biologically compatible material comprises one or more first pharmaceutical products, active and/or therapeutic ingredients designed to be released into a patient's tissues adjacent to the device.

11. A device according to claim 10, in which said biologically compatible material is porous and can have one or more pharmaceutical products, active and/or therapeutic ingredients, the same as or different to the one or more first pharmaceutical products, active and/or therapeutic ingredients, added to it.

12. A device according to claim 10, in which said pharmaceutical products, active and/or therapeutic ingredients comprise one or more of the following products: antibiotics, gentamicin, vancomycin, antiseptics, antimycotics, chemotherapy drugs, or active ingredients.

13. A device according to claim 1, in which said device is made from biologically compatible material which has no pharmaceutical products, active and/or therapeutic ingredients added to it.

14. A device according to claim 1, in which said device is made from biologically compatible material comprising materials chosen from metals, metal alloys, organic metals, ceramics, glass, or plastic.

15. A device according to claim 1, in which said device is made from biologically compatible material comprising a plastic chosen from thermoplastic polymers, acrylic resins, including all the copolymers and acrylic alloys, polyethylene, or polypropylene.

16. A device according to claim 15, in which said plastic is heat-formed by injection molding or by blow molding.

17. The device of claim 1, comprising a biologically compatible material, wherein said material comprises a combination of bone cement with one or more of the materials chosen from metals, metal alloys, organic metals, ceramics, glass, or plastic.

18. The device of claim 1, comprising a biologically compatible material, wherein said material comprises a combination of bone cement with one or more of the materials chosen from thermoplastic polymers, acrylic resins, including all the copolymers and acrylic alloys, polyethylene, or polypropylene.

* * * * *